US011953470B2

(12) United States Patent
Monkul et al.

(10) Patent No.: US 11,953,470 B2
(45) Date of Patent: Apr. 9, 2024

(54) AUTOMATIC FUNNEL CONTROL DEVICE

(71) Applicant: YEDITEPE UNIVERSITESI, Istanbul (TR)

(72) Inventors: Mehmet Murat Monkul, Istanbul (TR); Senay Yenigun, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 717 days.

(21) Appl. No.: 17/059,502

(22) PCT Filed: May 10, 2019

(86) PCT No.: PCT/TR2019/050319
§ 371 (c)(1),
(2) Date: Nov. 30, 2020

(87) PCT Pub. No.: WO2019/231425
PCT Pub. Date: Dec. 5, 2019

(65) Prior Publication Data
US 2021/0208040 A1 Jul. 8, 2021

(30) Foreign Application Priority Data
May 31, 2018 (TR) .................... 2018/07765

(51) Int. Cl.
*G01N 3/24* (2006.01)
*G01N 1/00* (2006.01)
*G01N 33/24* (2006.01)

(52) U.S. Cl.
CPC ................. *G01N 3/24* (2013.01); *G01N 1/00* (2013.01); *G01N 33/24* (2013.01); *G01N 2001/002* (2013.01); *G01N 2203/0284* (2013.01)

(58) Field of Classification Search
CPC . B01D 29/085; B01L 9/00; B01L 9/50; B67C 11/02; G01N 1/00; G01N 1/10;
(Continued)

(56) References Cited

U.S. PATENT DOCUMENTS

| 109,360 A | * | 11/1870 | Warth | ............... F16K 27/003 |
| | | | | 141/334 |
| 3,221,560 A | * | 12/1965 | Kosa | ................. G01N 11/02 |
| | | | | 222/161 |
| 2011/0146671 A1 | * | 6/2011 | Liu | ................. A61K 36/886 |
| | | | | 128/200.23 |

FOREIGN PATENT DOCUMENTS

| CN | 103344538 A | * | 10/2013 | ............. G01N 15/08 |
| CN | 203630014 U | * | 6/2014 | ............. G01N 15/08 |

(Continued)

OTHER PUBLICATIONS

Eagle Signal brand, B866-100/B866-500 Dial Set Timer Manual No. 702572-002, Danahr Industrial Controls (Year: 2004).*

*Primary Examiner* — David L Singer
(74) *Attorney, Agent, or Firm* — Bayramoglu Law Offices LLC

(57) ABSTRACT

A funnel control device is fixed on a shear box or respective cells in various soil mechanics/dynamics testing devices, and the funnel control device enables to produce soil samples to be tested by discharging a soil through a funnel into a sample preparation mold at a given axis and rate. The funnel control device includes at least one supporting body for being placed on the soil mechanics/dynamics testing device, at least one holder, wherein the at least one holder is provided on the at least one supporting body to be movable in vertical axis and the funnel is placed on the at least one holder, at least one driving member, wherein the at least one (Continued)

driving member is located in or on the at least one supporting body and is used for moving the at least one holder in the vertical axis.

21 Claims, 5 Drawing Sheets

(58) Field of Classification Search
CPC ............ G01N 1/286; G01N 2001/002; G01N 2001/1006; G01N 2203/0284; G01N 2203/0298; G01N 3/24; G01N 33/24
See application file for complete search history.

(56) References Cited

FOREIGN PATENT DOCUMENTS

| | | | | | |
|---|---|---|---|---|---|
| CN | 203630014 | U | | 6/2014 | |
| CN | 203639321 | U | * | 6/2014 | ............ C03B 20/00 |
| CN | 203916708 | U | * | 11/2014 | ................ B01L 9/00 |
| CN | 203916708 | U | | 11/2014 | |
| CN | 104697828 | A | * | 6/2015 | ............... G01N 1/28 |
| CN | 106053184 | A | * | 10/2016 | ............... G01N 1/28 |
| CN | 106124254 | A | * | 11/2016 | ............... G01N 1/20 |
| CN | 206295977 | U | * | 7/2017 | ................ B01L 9/00 |
| CN | 107067920 | A | * | 8/2017 | ............ G09B 23/24 |
| CN | 107067920 | A | | 8/2017 | |
| CN | 107225009 | A | | 10/2017 | |
| CN | 107225009 | A | * | 10/2017 | ................ B01L 9/00 |
| CN | 107510971 | A | * | 12/2017 | ........... B01D 29/085 |
| CN | 107510971 | A | | 12/2017 | |
| CN | 107782593 | A | * | 3/2018 | ............... G01N 1/28 |
| KR | 101011825 | B1 | * | 2/2011 | ............... G01N 3/24 |

\* cited by examiner

AUTOMATIC FUNNEL CONTROL DEVICE

CROSS REFERENCE TO THE RELATED APPLICATIONS

This application is the national stage entry of International Application No. PCT/TR2019/050319, filed on May 10, 2019, which is based upon and claims priority to Turkish Patent Application No. 2018/07765, filed on May 31, 2018, the entire contents of which are incorporated herein by reference.

TECHNICAL FIELD

The present invention relates to an automatic funnel device which is fixed on a testing device and which is used for transferring the soil sample to a shear box in a standardized manner by gradually pulling the funnel located thereon on a fixed and symmetrical vertical axis. The funnel method is a method used for preparing the soil samples in various tests performed in Soil Mechanics and Soil Dynamics tests of Civil Engineering.

BACKGROUND

In the state of the art, specimens for experiments are prepared and tested in laboratory in order to examine the stress-strain behaviors and determine the strength of granular soils (e.g. sand, silty sand, silt etc.) under static or dynamic loads, to determine various soil parameters precisely or to investigate the effects of various factors on static and dynamic soil behavior. Since it is very difficult and requires expensive methods to obtain undisturbed samples from in-situ of the said granular soils, various techniques are used for preparation of samples in the laboratory. One of the most commonly used one of these methods is the funnel method.

In the current art, in order to produce samples in any soil mechanics testing apparatus (e.g. direct shear, simple shear or triaxial compression test, etc.), generally a kitchen type plastic funnel is manually aligned with the center of the base of the concerned testing apparatus (e.g. shear box). Then, after the soil intended to be tested is poured into the funnel, the funnel is manually lifted upwards along the vertical symmetry axis. Thus, the soil is discharged through the funnel into a mold and a soil sample is produced for testing. However, in the state of the art, during the duplicating tests, the quality of the sample is affected and different test results may be obtained due to problems such as shaking and misalignment of the funnel when the funnel is being manually lifted upwards by the user and aligning the funnel to the shear box with respect to the vertical symmetry axis. In order for the tests to be reproducible, it is necessary and mandatory to prepare the samples in exactly the same manner in all experiments. This brings along a very demanding and long time-consuming working process and the requirement that the person who will perform the test acquires precise manual skills. It is not possible to fully control this manually performed process and thus it becomes difficult to reach reliable test results. In addition, the funnel lifting rate and duration and the height at which the soil is poured into the funnel cannot be controlled.

The current problems in the conventional funnel technique (prior art) mentioned above and being applied up to date in the literature can be listed as follows: 1) inability to control the lifting speed of the funnel which is manually lifted, 2) failure to align the funnel the position of which is manually adjusted with respect to the vertical symmetry axis of the sample, 3) inability to control the pouring height of the soils into the funnel, 4) inability to control human errors (e.g. hand shaking, discontinuities and changes in funnel lifting speed, axial dislocation during lifting, etc.). It has been determined that each of these problems has an impact on the quality and density index parameters of the soil samples to be produced (void ratio, relative density, etc.).

Chinese document numbered CN203916708U, an application in the state of the art, discloses a funnel rack which is used in laboratories and can adjust the height of the funnel. In the said document, there is a middle plate including a hole into which the funnel will be placed and bracket feet around the middle plate. The height of the funnel is adjusted by tightening the inclined end region of the funnel on the desired position on the hole by means of bolts. In the said document, the invention is used for limiting downward movement of the funnel, and it does not disclose any arrangement for pulling (lifting) the funnel upwards.

SUMMARY

The objective of the present invention is to provide an automatic funnel control device which is used in various soil mechanics/dynamics testing equipment (e.g. direct shear, simple shear or triaxial compression test, etc.) and which is intended for transferring the soil in the funnel placed thereon to the shear box for each test in a standardized manner.

Another objective of the present invention is to provide an automatic funnel control device which is used in various soil mechanics/dynamics testing equipment for aligning the funnel placed on the shear box/base plate with the shear box for each test in a standardized manner.

A further objective of the present invention is to provide an automatic funnel control device which is used for moving the funnel automatically at the determined seconds and determined distance without manual intervention.

Another objective of the present invention is to provide an automatic funnel control device wherein the distance between the funnel and shear box is short and which thus prevents splashing of the sample.

A further objective of the present invention is to provide an automatic funnel control device which can control the pouring height of the soil into the funnel by means of the attachable/removable parts in the funnel body.

Another objective of the present invention is to prevent various human errors—such as shaking of hands in the course of the funnel method, speed change and discontinuities during lifting funnel, axial dislocation during lifting from affecting the soil samples to be formed and the test results.

BRIEF DESCRIPTION OF THE DRAWINGS

An automatic funnel device developed to fulfill the objective of the present invention is illustrated in the accompanying figures wherein.

Figure 1:
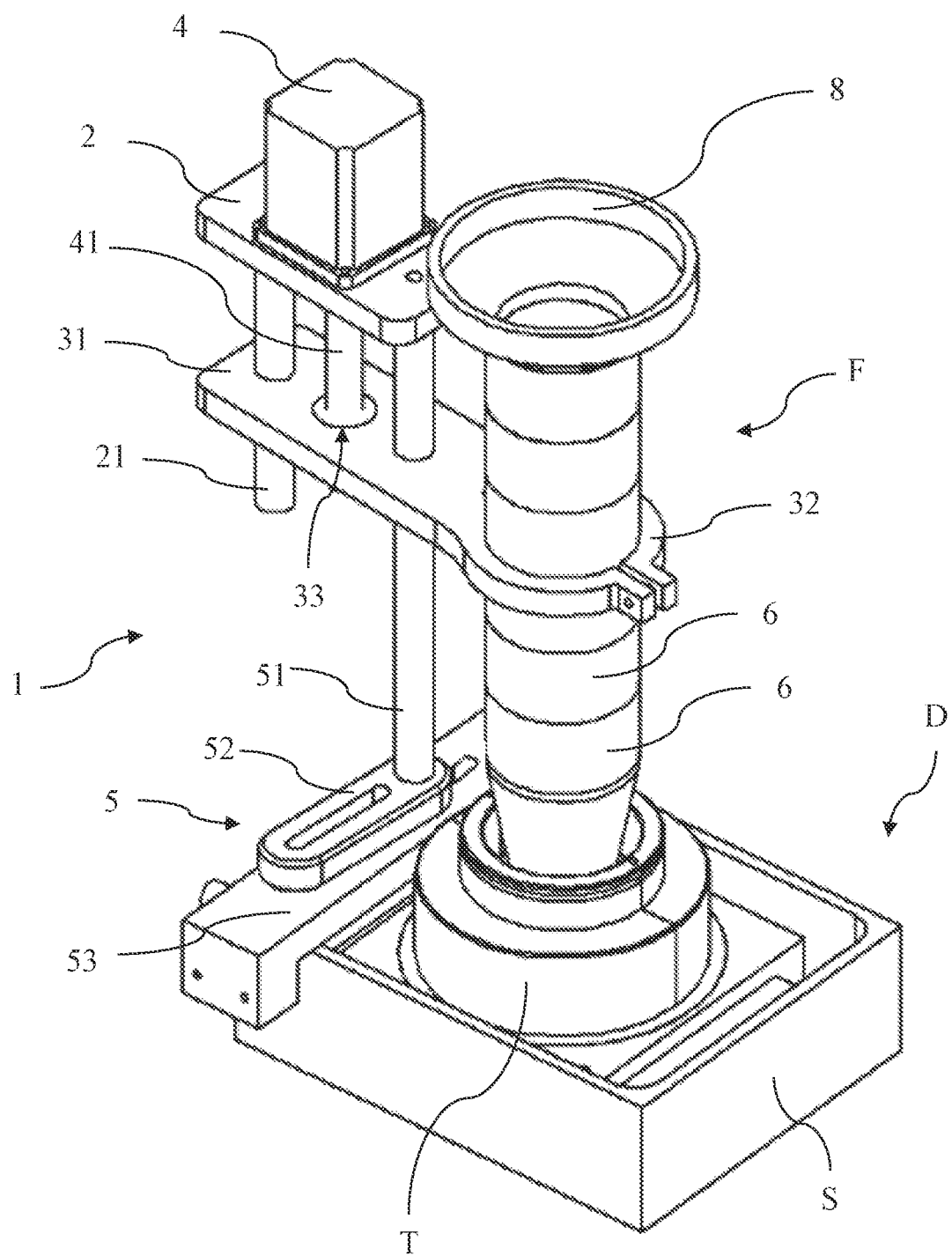
FIG. 1 is a front perspective view of the inventive automatic funnel control device mounted on the testing device.
Figure 2:
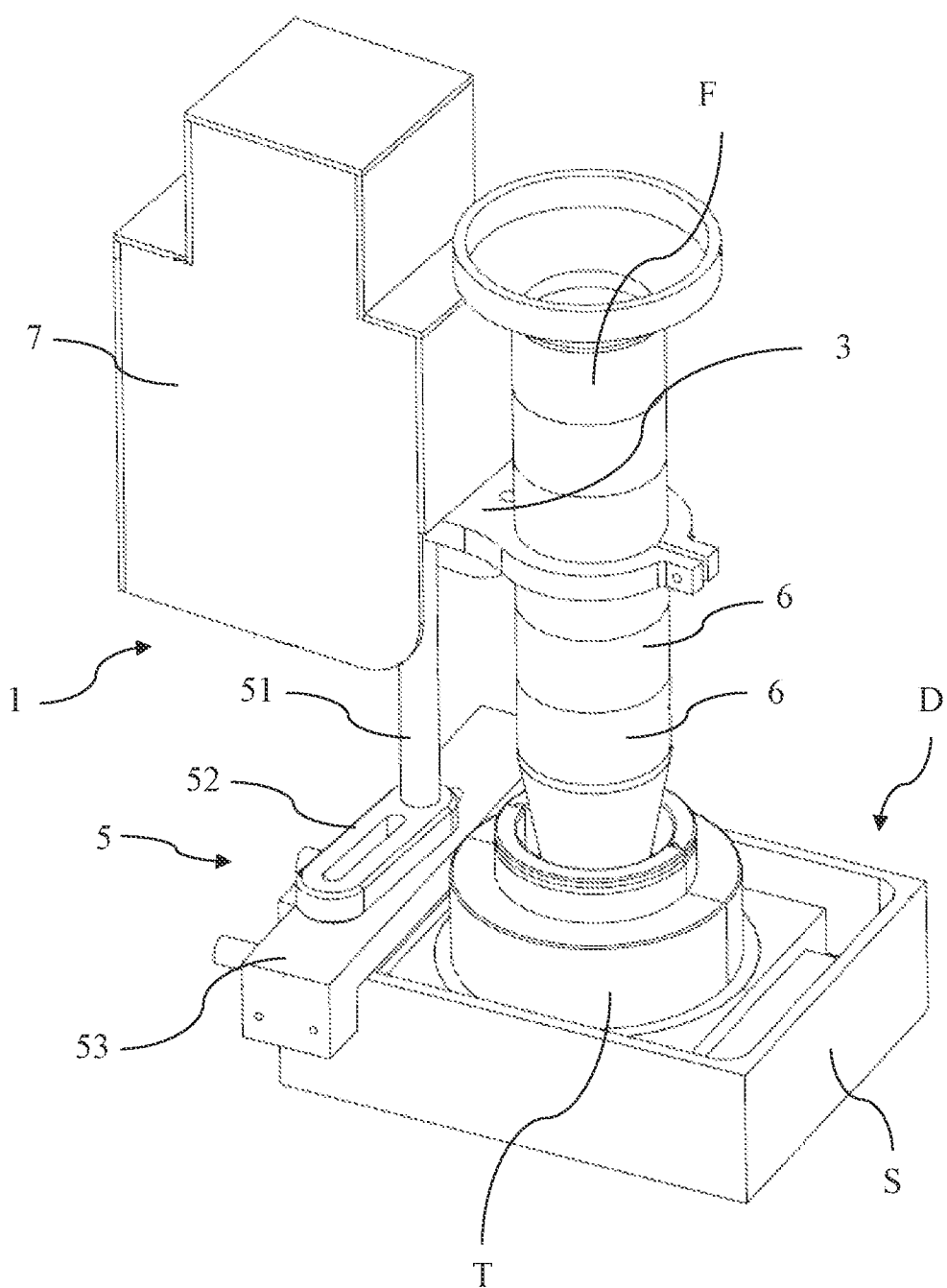
FIG. 2 is a front perspective view of the inventive automatic funnel control device with the protection cover mounted on the testing device.
Figure 3:
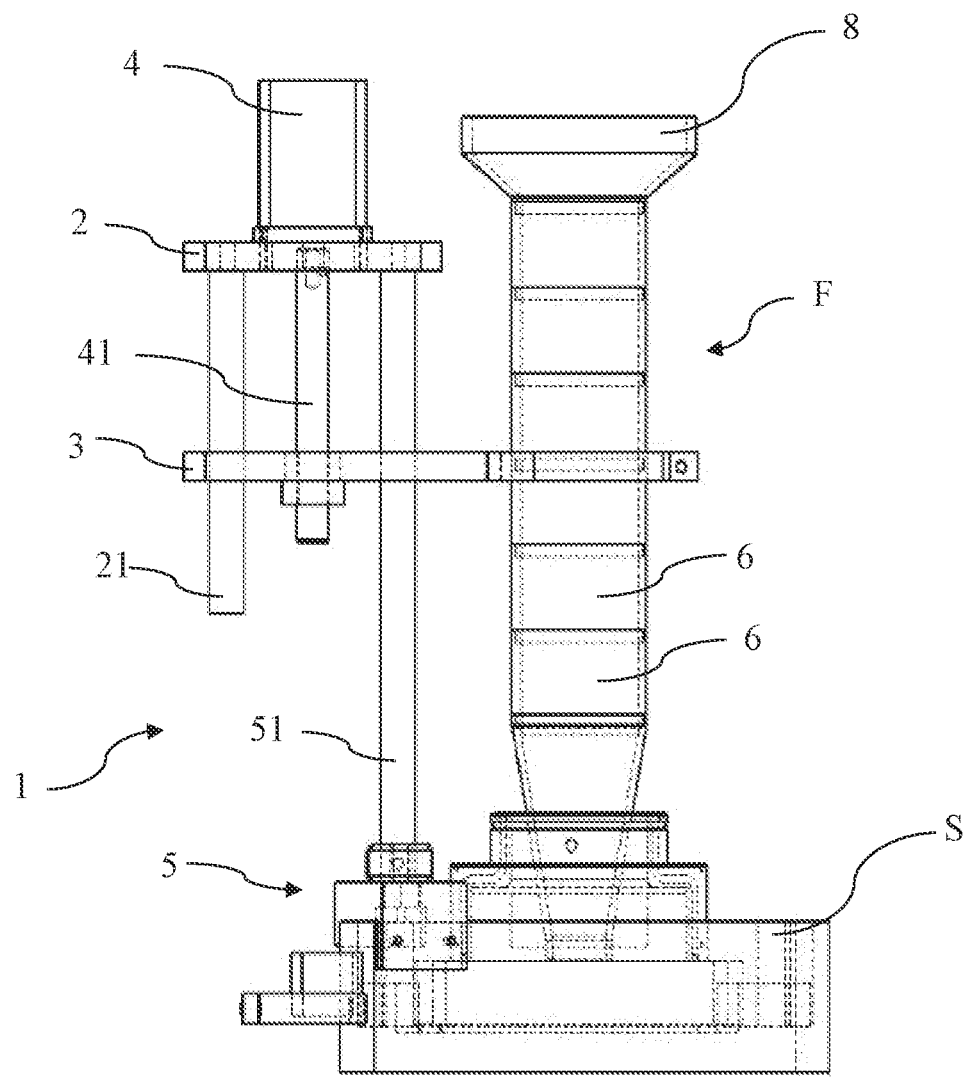
FIG. 3 is a front view of the inventive automatic funnel control device mounted on the testing device.
Figure 4:
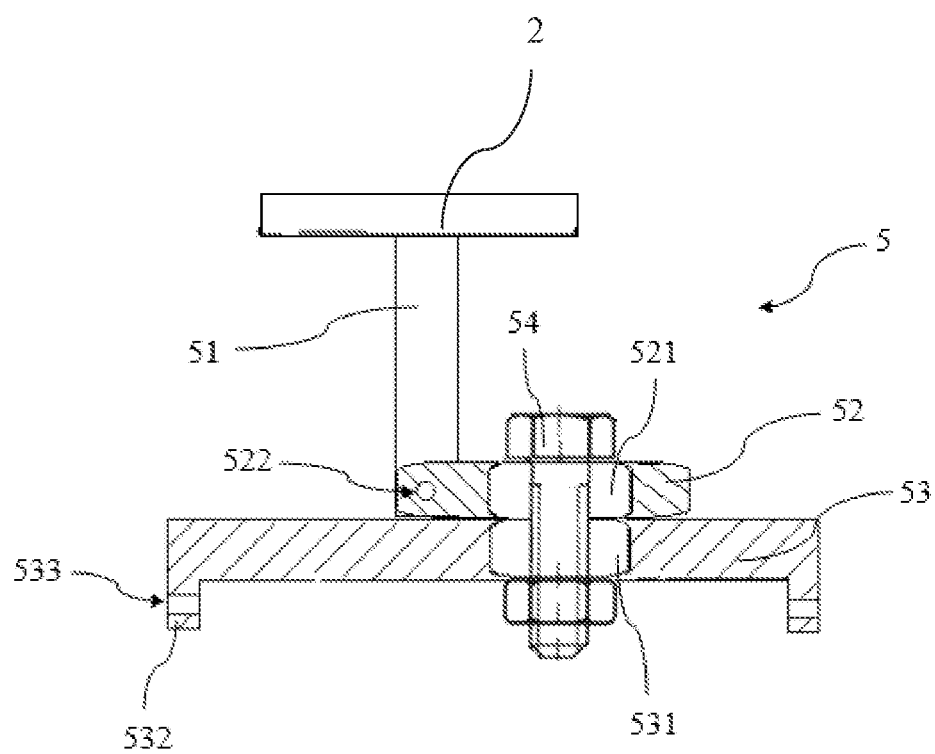
FIG. 4 shows a side view and a detail cross-section view of the connection system in the inventive automatic funnel control device.

The components in the figures are each given reference numbers as follows:
1. Funnel control device
   2. Supporting body
      21. Secondary rod
   3. Holder
      31. Connecting body
      32. Slot
      33. Movement hole
   4. Driving member
      41. Movement shaft
   5. Connection system
      51. Rod
      52. Adjustment part
         521. First channel
         522. Screw hole
      53. Fixing bracket
         531. Second channel
         532. Mounting protrusion
         533. Mounting adjustment hole
      54. Adjustment connection member
   6. Funnel ring
   7. Protection cover
   8. Funnel head
   U. Testing device
   F. Funnel
   S. Shear box
   T. Sample preparation mold

DETAILED DESCRIPTION OF THE EMBODIMENTS

A funnel control device (1), which is used by being fixed on the shear box (S) or its respective cells in various soil mechanics/dynamics testing devices (D), and which is used to produce soil samples to be tested by discharging the soil through a funnel (F) into the sample preparation mold (T) at a given axis and rate, comprises
   at least one supporting body (2) for being placed on the testing device (D),
   at least one driving member (4) which is located in or on the supporting body (2) and is used for producing drive force,
   at least one holder (3) which is connected to the driving member (4), can move in the vertical direction with the drive force of the driving member (4), and on which the funnel (F) is placed.

The funnel control device (1) according to the invention is used upon being fixed on a testing device (D) and it is used to prepare the sample in the funnel (F) at the desired standard each time by moving the funnel (F) placed thereon in the vertical axis on the testing device (D). The supporting body (2) in the funnel control device (1) according to the invention is fixed on the testing device (D). The holder (3) is mechanically connected to the driving member (4) on the supporting body (2) and has a slot in which the funnel (1') is to be placed at the outer part of the supporting body (2). The holder (3) is moved downward or upward in the vertical direction together with the funnel (F) placed thereon by the movement received from the driving member (4). By lifting (pulling) the funnel (F) upwards, the sample in the funnel (F) is prepared in the same manner each time on the sample testing device (D). With the funnel control device (1), the sample preparation step of the testing process, which must be laborious and rigorous, takes a long time and requires manual skill and experience, can be easily completed; and the results of the test are reproducible and reliable as it enables to prepare identical samples. The results of the tests conducted in this way are more reliable in terms of both engineering practice and design, and research. By means of the funnel control device (1), various combinations, in which the soils are poured from different heights and the funnel (F) is lifted at different speeds are tested by the inventors, and their effects on sample density and liquefaction resistance, which is of great importance in civil engineering, can be determined. In addition, axial dislocations in the stress-strain relationship observed in the test results of the samples which are not prepared symmetrically are prevented and thus more reliable test results are obtained.

In one embodiment of the present invention, the holder (3) comprises at least one connecting body (31) connected with the driving member (4) and a slot (32) on which the funnel (F) is placed. In another embodiment of the present invention, the slot (32) is in the form of a clamp, and by tightening the clamp, the slot (32) can be adjusted according to the funnels of different diameters.

In one embodiment of the present invention, the funnel control device (1) comprises a connection system (5), which is used for fixing the supporting body (2) onto the testing device (1)) and adjusting its position, and which has
   at least one rod (51) which is preferably fixed to the base of the supporting body (2),
   at least one adjustment part (52) which is connected onto the rod (51) and has thereon a first adjustment channel (521) in the form of a channel-shaped hole,
   at least one fixing bracket (53) which is used upon being fixed onto the testing device (D) and has thereon a second adjustment channel (531) in the form of a channel-shaped hole,
   at least one adjustment connection member (54), which passes through the first adjustment channel (521) and the second adjustment channel (531), and which is used for connecting the adjustment part (52) to the fixing bracket (53) at the adjusted position.

In one embodiment of the invention, there is provided a connection system (5) which is used to fix the supporting body (2) on the testing device (D) and to align the supporting body (2) on the test device (D) to the portion of the funnel (F) to which the sample is intended to be poured. The connection system (5) comprises a rod (51) extending from the supporting body (2), an adjustment part (52) connected to the rod (51), and a fixing bracket (53) fixed to the testing device (D). There are channels (first adjustment channel (521) and second adjustment channel (531)) on the adjustment part (52) and the fixing bracket (53), and there is an adjustment connection member (54) that passes through the channels and can move linearly in the channels. By aligning the funnel (F) placed in the holder to the desired pouring point (preferably a porous stone) on the testing device ED), the adjustment connection member (54) is tightened to fix the supporting body (2) onto the fixing bracket (53). In one embodiment of the invention, the adjustment connection member (54) is comprised of a bolt and nut.

In one embodiment of the invention, the rod (51) is cylindrical, and the adjustment part (52) is rotatably fixed on the rod (51). In another embodiment of the invention, the adjustment part (52) includes thereon a screw hole (522) that opens towards the rod (51), and, when the supporting body (2) comes to the desired position, the connection member (screw) is passed through the said screw hole (522) thereby fixing the adjustment part (52) onto the rod (51).

In one embodiment of the present invention, there are two mounting protrusions (532) on the opposite ends of the base portion of the fixing bracket (53) that is fixed to the testing device (D); and there is a mounting adjustment hole (533) on each of these mounting protrusions (532). The mounting protrusions (532) can be fixed by clamping onto the testing device (DD) by means of the connection members (screws, bolts, allen screws, etc.) which are passed through the mounting adjustment holes (533).

In one embodiment of the invention, the driving member (4) is a motor. In another embodiment of the invention, the driving member (4) is a step motor. In another embodiment of the invention, the driving member (1) is a hydraulic piston. In a further embodiment of the invention, the driving member (4) is a pneumatic piston.

In one embodiment of the invention, the supporting body (2) is in the form of a plate.

One embodiment of the invention includes the following which enables to transmit drive force from the driving member (4) to the holder (3):
  at least one threaded movement hole (33) which is located on the holder (3), and
  a movement shaft (41) which is connected to the output of the driving member (4), and which passes through the threaded movement hole (33), and includes thereon threads.

The movement shaft (41) provided in one embodiment of the invention is connected to the rotary movement output of the driving member (4) it is threaded. The movement shaft (41) passes through the threaded movement hole (33) provided on the holder (3) in a threaded connection. With the actuation of the driving member (4) (motor), the movement shaft (41) rotates about its own axis, and, thanks to the threaded connection, the holder (3) moves upwards or downwards relative to the direction of rotation of the driving member (4).

In one embodiment of the present invention, the rod (51) fixed to the supporting body (2) passes through a hole on the holder (3) and prevents the rotation of the holder (3) by means of the movement shaft (41) and ensures that the holder (3) only moves linearly.

In another embodiment of the present invention, a secondary rod (21) extends from the supporting body (2) and passes through the holder (3). The secondary rod (21) prevents the rotation of the holder (3) as a result of the rotating movement of the movement shaft (41) and enables the holder (3) to move only linearly in the vertical direction.

In another embodiment of the present invention, there is a gear box between the driving member (4) and the holder (3), and the force is transferred from the motor to the holder (3).

Figure 5:
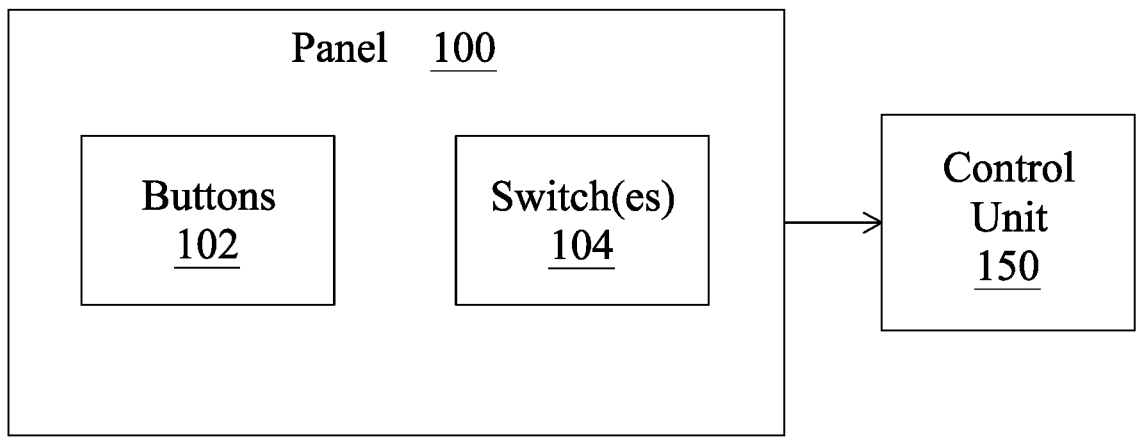
FIG. 5 is a high-level diagram of a control unit.

In one embodiment of the present invention, as illustrated in FIG. 5, there is at least one control unit 150 that controls the driving member (4) by the data entered by the user.

In one embodiment of the present invention, as illustrated in FIG. 5, there is provided at least one panel 100 with buttons 102 for the user to operate and shut down the system, and to enter the funnel (F) lifting speed and time data. In one embodiment of the invention, the panel is located on the supporting body (2). In another embodiment of the invention, the panel is connected to the driving member (4) by means of cables.

In one embodiment of the invention, as illustrated in FIG. 5, there is provided a 10 step switch or switches 104 on the panel 100 enabling to adjust the time to 15, 30, 45, 60, 75, 90, 105, 120, 135 and 150 seconds. Thus, the funnel (F) lifting speed, which has an impact on the density and porosity rate of the sample that will be produced, is taken under control. In one embodiment of the invention, the above given times and numbers of step are changed thereby different funnel lifting times and speeds are provided.

In one embodiment of the present invention, the testing device (D) is a soil mechanics/dynamics testing apparatus used for the soil sample, and the funnel control device (1) is fixed onto the shear box (S) or an equivalent piece of equipment of the soil mechanics/dynamics testing apparatus. The funnel (F) is placed in the middle of the base of a sample preparation mold (T) which is provided in the soil mechanics/dynamics testing device (D) and which has a porous stone therein. The funnel (F) used in the soil mechanics/dynamics testing device (D) is preferably made of an aluminum material.

In one embodiment of the invention, there are adjustment rings, which are provided on the funnel (F), and which enable to adjust the height of pouring the soil into the funnel, and can be mounted to or removed from the funnel (F) at various heights and numbers. By means of the adjustment rings (6), the height of pouring the soil into the funnel, which affects the sample density and thus the test results, is also adjusted. In another embodiment of the invention, the height of each adjustment ring (6) is 37 mm and the number of the adjustment rings is six. In another embodiment of the invention, there is provided a funnel head (8), which is mounted on top of the aluminum portion of the funnel (F) and has a diameter greater than the adjustment rings provided below it, and whose purpose is to allow the soil to be easily poured into the funnel.

A funnel control device (1), which, for a testing device (D) such as a soil mechanics/dynamics test, is used for transferring the sample in a funnel (F) to the testing device (D); comprises
  at least one supporting body (2) for being placed on the testing device (D),
  at least one holder (3) which is fixed on the supporting body (2) and on which the funnel (F) is placed,
  at least one driving member (4) which is connected to the supporting body (2) and used for moving the supporting body (2) in vertical axis.

In the said funnel control device (1), the driving member (4) is placed on the testing device (D), and the driving member (4) moves the holder (3), on which the funnel (F) is placed, together with the supporting body (2).

The funnel control device (I) to be mounted on the testing device (D) is firstly adjusted, by means of the connection system (5) thereon, according to the testing device (D). Then, it is arranged on the testing device (D) and tightened via connection members (screws, etc.) via the mounting adjustment hole (533) of the fixing bracket (53). In order to ensure that the test results are reliable and reproducible, it is of great importance that the aluminum funnel (F) is placed exactly in the center. The sample preparation mold (T) used for this is placed on top of the porous stone wherein the test is to be prepared, and thus the aluminum funnel (F) is ensured to be placed exactly in the center. Afterwards, the steps that will make the test system ready for the test are completed. The funnel (F) will adopt the porous stone as the center and transmit the soil contained therein upwards by 40 mm from this point at a constant funnel lifting speed in a period of time selected from 15 to 150 seconds. When the funnel control device (1) is ready to prepare the sample, the button on the panel is pressed, and thereby the device will come to the required position. After the sample is discharged into the funnel (H), the funnel lifting time is selected in seconds from the switch in the panel. In one embodiment of the invention, the funnel lifting time is selected in minutes or hours from the switch in the panel. In one embodiment of the invention, the funnel lifting speed is selected in from the switch in the panel instead of the funnel lifting time. When the start button is pressed, the funnel (F) is lifted upwards 4 cm in the specified time interval, and thus the soil sample is deposited in a controlled manner without undergoing any disturbance. In one embodiment of the invention, the distance of lifting the funnel upward in the specified time interval can be adjusted by the user.

In the preferred embodiment of the invention, precision of the funnel control device (1) is ±0.05 mm. The electricity used by the funnel control device (1) is 220 vAc and the control of the system is controlled by 24 vDc 5 Amp current.

In one embodiment of the invention, there is provided at least one protection cover (7) which is used to cover the driving member (4) and the supporting body (2), and to protect the driving member (4) and the supporting body (2) against external factors. The protection cover (7) is preferably fixed on the supporting body (2).

The invention claimed is:

1. A funnel control device, wherein the funnel control device is fixed on a testing device, comprising:
   at least one supporting body, wherein the at least one supporting body is placed on the testing device;
   at least one driving member, wherein the at least one driving member is located in or on the at least one supporting body and the at least one driving member is configured to produce a drive force;
   at least one holder, wherein the at least one holder is connected to the at least one driving member, the at least one holder moves in a vertical direction with the drive force of the at least one driving member, and a funnel is placed on the at least one holder; and
   a connection system, wherein the connection system is configured to fix the at least one supporting body onto the testing device and is configured to adjust a position of the at least one supporting body, the connection system including:
      at least one rod, wherein the at least one rod is on the at least one supporting body,
      at least one adjustment part, wherein the at least one adjustment part is connected onto the at least one rod and the at least one adjustment part comprises a first adjustment channel in a form of a channel-shaped hole, and
      at least one fixing bracket, wherein the at least one fixing bracket is fixed onto the testing device and the at least one fixing bracket comprises a second adjustment channel in the form of the channel-shaped hole.

2. The funnel control device according to claim 1, wherein the at least one holder comprising at least one connecting body connected with the at least one driving member and a slot, wherein the funnel is placed on the slot.

3. The funnel control device according to claim 2, wherein the slot is in a form of a clamp.

4. The funnel control device according to claim 1, wherein the at least one supporting body is in a form of a plate.

5. The funnel control device according to claim 1, comprising at least one adjustment connection member, wherein the at least one adjustment connection member passes through the first adjustment channel and the second adjustment channel, and the at least one adjustment connection member is configured to connect the at least one adjustment part to the at least one fixing bracket at an adjusted position.

6. The funnel control device according to claim 1, wherein the at least one adjustment part is rotatably fixed on the at least one rod.

7. The funnel control device according to claim 1, comprising a screw hole, wherein the screw hole is provided on the at least one adjustment part and the at least one adjustment part opens towards the at least one rod.

8. The funnel control device according to claim 1, wherein the at least one fixing bracket comprises two mounting protrusions on opposite ends of a base portion of the at least one fixing bracket and the at least one fixing bracket further comprises a mounting adjustment hole on each of the two mounting protrusions.

9. The funnel control device according to claim 1, comprising:
   at least one threaded movement hole, wherein the at least one threaded movement hole is located on the at least one holder, and
   a movement shaft, wherein the movement shaft is connected to an output of the at least one driving member, and the movement shaft passes through the at least one threaded movement hole, and the movement shaft comprises threads on the movement shaft, wherein the movement shaft transmits the drive force from the driving member to the at least one holder.

10. The funnel control device according to claim 1, wherein the at least one rod passes through a hole on the at least one holder and the at least one rod ensures the at least one holder only moves linearly.

11. The funnel control device according to claim 1, comprising at least one secondary rod, wherein the at least one secondary rod extends from the at least one supporting body and the at least one secondary rod passes through the at least one holder and the at least one secondary rod ensures the at least one holder only moves linearly.

12. The funnel control device according to claim 1, wherein the at least one driving member is a motor, a step motor, a hydraulic piston or a pneumatic piston.

13. The funnel control device according to claim 1, comprising at least one control unit for controlling the at least one driving member by data entered by a user.

14. The funnel control device according to claim 13, comprising at least one panel with buttons and switches, wherein the at least one panel is configured to receive funnel lifting time data and to transmit the funnel lifting time data to the at least one control unit.

15. The funnel control device according to claim 14, wherein the at least one panel is provided with a 10-step switch for adjusting a time to 15, 30, 45, 60, 75, 90, 105, 120, 135 and 150 seconds.

16. The funnel control device according to claim 1, comprising at least one protection cover, wherein the at least one protection cover is configured to cover the at least one driving member and the at least one supporting body, and the at least one protection cover is configured to protect the at least one driving member and the at least one supporting body against external factors.

17. The funnel control device according to claim 1, comprising at least one funnel head, wherein the at least one funnel head is mounted on a top of an aluminum portion of the funnel and a diameter of the at least one funnel head is greater than a diameter of the funnel, and the at least one funnel head is configured to pour soil into the funnel.

18. The funnel control device according to claim 1, wherein the funnel control device is fixed on a soil mechanics/dynamics testing device, wherein the soil mechanics/dynamics testing device is configured to test soil samples.

19. The funnel control device according to claim 1, wherein the funnel control device is fixed on a shear box of a soil mechanics/dynamics testing device, wherein the shear box of the soil mechanics/dynamics testing device is configured to test soil samples.

20. A funnel control device, wherein the funnel control device is fixed on a testing device, comprising:
- at least one supporting body, wherein the at least one supporting body is placed on the testing device;
- at least one holder, wherein the at least one holder is fixed on the at least one supporting body and a funnel is placed on the at least one holder;
- at least one driving member, wherein the at least one driving member is connected to the at least one supporting body and the at least one driving member is configured to move the at least one supporting body and the at least one driving member is configured to move the at least one holder in a vertical axis; and
- a connection system, wherein the connection system is configured to fix the at least one supporting body onto the testing device and is configured to adjust a position of the at least one supporting body, the connection system including:
  - at least one rod, wherein the at least one rod is on the at least one supporting body,
  - at least one adjustment part, wherein the at least one adjustment part is connected onto the at least one rod and the at least one adjustment part comprises a first adjustment channel in a form of a channel-shaped hole, and
  - at least one fixing bracket, wherein the at least one fixing bracket is fixed onto the testing device and the at least one fixing bracket comprises a second adjustment channel in the form of the channel-shaped hole.

21. A funnel control device, wherein the funnel control device is fixed on a testing device, comprising:
- at least one supporting body, wherein the at least one supporting body is placed on the testing device;
- at least one driving member, wherein the at least one driving member is located in or on the at least one supporting body and the at least one driving member is configured to produce a drive force; and
- at least one holder, wherein the at least one holder is connected to the at least one driving member, the at least one holder moves in a vertical direction with the drive force of the at least one driving member, and a funnel is placed on the at least one holder; and
- circular adjustment rings, wherein the circular adjustment rings are provided on an aluminum portion of the funnel, and the circular adjustment rings adjust a height of pouring a soil into the funnel, and the circular adjustment rings are mounted to or removed from the funnel at various heights and various numbers.

* * * * *